United States Patent [19]

Kelly

[11] Patent Number: 4,551,288

[45] Date of Patent: Nov. 5, 1985

[54] PROCESSES FOR THE PREPARATION OF LIPOSOME DRUG DELIVERY SYSTEMS

[75] Inventor: Lawrence A. Kelly, Morris Plains, N.J.

[73] Assignee: Sandoz, Inc., E. Hanover, N.J.

[21] Appl. No.: 648,652

[22] Filed: Sep. 7, 1984

Related U.S. Application Data

[63] Continuation-in-part of Ser. No. 408,188, Aug. 16, 1982, abandoned.

[51] Int. Cl.[4] .......................... B01J 13/02; A61K 9/50
[52] U.S. Cl. .................................. 264/4.6; 210/198.2; 264/4.1; 424/1.1; 436/829
[58] Field of Search ..................... 264/4.1, 4.6; 424/38; 436/829

[56] References Cited

U.S. PATENT DOCUMENTS

| | | | |
|---|---|---|---|
| 3,155,590 | 11/1964 | Miller et al. | 428/402.2 X |
| 3,657,144 | 4/1972 | Yoshida | 264/4.6 X |
| 4,089,801 | 5/1978 | Schneider | 264/4.1 |
| 4,235,871 | 11/1980 | Papahadjopoulos et al. | 424/38 X |
| 4,308,166 | 12/1981 | Marchetti et al. | 264/4.6 X |
| 4,310,506 | 1/1982 | Baldeschwieler et al. | 264/4.1 X |
| 4,356,167 | 10/1982 | Kelly | 424/38 |

OTHER PUBLICATIONS

Rhoden et al.: "Formation of Unilamellar Lipid Vesicles of Controllable Dimensions by Detergent Dialysis", Biochemistry, vol. 18, No. 19 (1979) pp. 4173-4176.

Primary Examiner—Richard D. Lovering
Attorney, Agent, or Firm—Gerald D. Sharkin; Robert S. Honor; Walter F. Jewell

[57] ABSTRACT

Process and apparatus for the production of medicament containing liposomes, comprising an aliphatic lipid-sterol-water lamellae, wherein a clear, mixed micellar medicament-detergent-aliphatic lipid-sterol sample is applied to a gel filtration column. The column effluent is continuously monitored to detect the liposome fraction eluted, which is collected. The free medicament, detergent, lipid and/or sterol may be recirculated back to the column.

18 Claims, 1 Drawing Figure

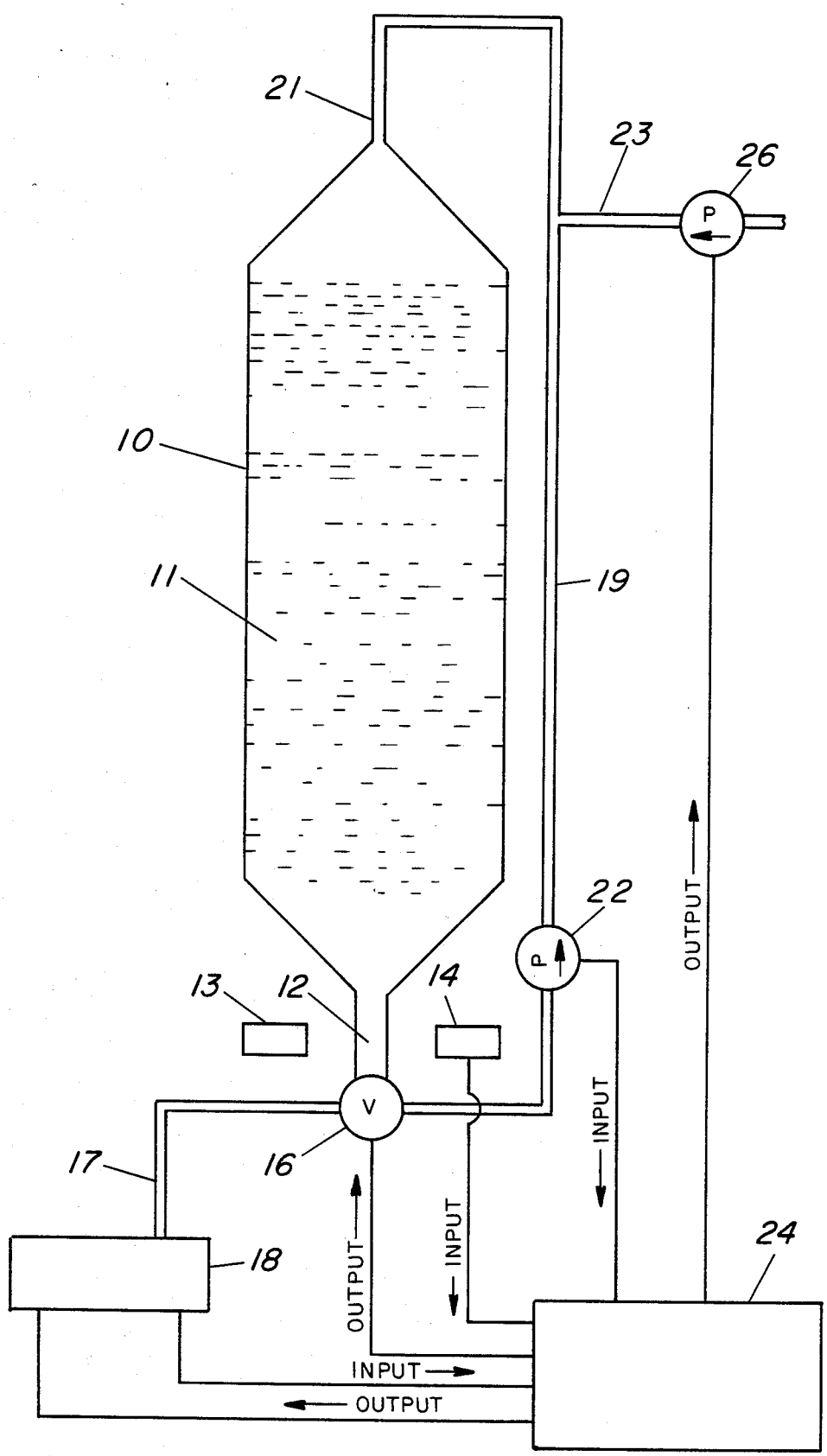

PROCESSES FOR THE PREPARATION OF LIPOSOME DRUG DELIVERY SYSTEMS

This application is a continuation-in-part of application Ser. No. 408,188 filed Aug. 16, 1982 and now abandoned.

BACKGROUND OF THE INVENTION

Liquid crystalline phases of lipids are known in the prior art. These phases are called liquid crystalline since they have degrees of order which are intermediate between the three dimensional order of a crystal and the random distribution of a liquid. These phases have order in one or two dimensions characterized by onion-skin or lamellar arrangements of the lipids when dispersed in water.

When liquid crystals are subjected to energy in the form of ultrasonic radiation, they can be broken down to single layer vessicles of small dimensions called liposomes.

In recent years encapsulation of various medicaments in phospholipid-chloesterol liposomes has been accomplished. The systems described are ternary systems of a phospholipid plus cholesterol and water. Basically, these systems are prepared by dissolving the phospholipid and cholesterol in a solvent which is evaporated to leave a thin film of lipid. The aqueous phase medicament is then added, which swells the cholesterol phospholipid mixture to encapsulate the medicament. Subsequent ultrasonic irradiation provides the liposomes.

Vanlerberghe et al. U.S. Pat. No. 4,217,344, discloses the preparation of dispersions of liposomes containing an active substance, which after size reduction by ultrasonic treatment, are separated from the dispersion by gel filtration.

Preparation of phospholipid-sterol liposomes by gel filtration without sonication has been described by J. Brunner et al. "Single Bilayer Vesicles Prepared Without Sonication Physico-Chemical Properties" Biochemica et Biophysica Acta, 455 (1976) 322–331.

Basically, the prior art preparation of phospholipid-sterol liposomes using gel filtration involved two major steps:

(1) The preparation of the liposome in the traditional fashion by,
 (a) Dissolving the lipid substances in organic solvents to evenly disperse the components, and then evaporating the solvent.
 (b) Adding water or other aqueous media containing drug to the lipid film to form the liposomes.

The liposome dispersion is then sonicated or not sonicated depending on the type of liposome desired.

(2) The liposome preparation is passed over a gel-filtration column to remove untrapped drug and to isolate liposomes of a uniform size.

In contrast, the present liposome process using gel filtration involves the following steps:

(1) Solubilization and homogeneous dispersion of drug and lipid components in a detergent (rather than organic solvent).

(2) Passage of the detergent solution over a gel-filtration column which removes the detergent, causing the formation of the liposome.

In the present invention the concentration of components may be in excess of that necessary for liposome formation. The liposome formed will be what is physically the most stable form. The present procedure may be made limiting by initially adjusting the concentration of the components. Thus, the present procedure allows for greater control over the final liposome composition than the prior art procedure.

SUMMARY OF THE INVENTION

This invention relates to processes and apparatus for the preparation of medicament delivery systems. It provides processes for the preparation of liposome medicament delivery systems, wherein a medicament is encapsulated in a liposome, comprising an aliphatic lipid-sterol-water lamellae.

Broadly, this invention provides a process for the production of medicament containing liposomes, comprising an aliphatic lipid-sterol-water lamallae, wherein a clear, mixed micellar medicament-detergent-aliphatic lipid-sterol sample is applied to a gel filtration column e.g. Sephadex G50. The column effluent is monitored to detect the liposome fraction eluted. On passage through the column a liquid crystalline (liposome) front comes off around the void volume. The liposomal fraction is collected. The free medicament, detergent, lipid and/or sterol may be recirculated back to the column.

Preferably, this invention provides a continuous process for the production of medicament containing liposomes, comprising an aliphatic lipid-sterol-water lamellae, wherein a clear, mixed micellar medicament-detergent-aliphatic lipid-sterol sample is applied to a gel filtration column e.g. Sephadex G50. The column effluent is continuously monitored to detect the liposome fraction eluted. On passage through the column a liquid crystalline (liposome) front comes off around the void volume. The liposomal fraction is collected. The free medicament, detergent, lipid and/or sterol are recirculated back to the column.

Certain medicaments in the liposome systems may be subject to alkaline degradation such as hydrolysis. Adjustment of the hydrogen ion concentration (pH) of these systems may be necessary to protect the medicaments from the alkaline degradation.

This invention provides an apparatus for the preparation of liposome medicament delivery systems which comprises a column having a loading end and a discharge end. The discharge end has photoelectric detection means in optical association therewith. The discharge end is in fluid communication with a multidirectional valve, which is switchable between a first conduit and a second conduit. The first conduit is in communication with a fluid collection device. The second conduit is in communication with the column loading end, an introductory circuit and a pump. A microprocessor is in electronic communication with the photoelectric detection means, the multidirectional valve, the fluid collection device and the pump, whereby the microprocessor controls fluid flow from the column by switching fluid flow to either the collection device or the column loading end, depending upon the input electronic signal received from the photoelectric device.

DESCRIPTION OF THE PREFERRED EMBODIMENTS

The aliphatic lipid may be any pharmacologically acceptable aliphatic surface-active compound which forms micelles in aqueous media when present in concentrations above the critical micelle concentration include the sodium and potassium salts of $C_4$ to $C_{18}$ saturated and unsaturated fatty acids, e.g., butyric acid, isovaleric acid, caproic acid, caprylic acid, lauric acid, myristic acid, palmitic acid, stearic acid, oleic acid, linoleic acid, linolenic acid, and their amides. Other pharmacologically acceptable aliphatic surface active agents may include glycerol containing phospholipids both natural and synthetic (containing choline, ethanolamine, serine or inositol), phosphotidyl glycerol and shingosine containing lipids such as shingomyelin, cardiolipin glucolipids, gangliosides and cerebrosides.

The sodium and potassium salts of $C_4$ to $C_{18}$ unsaturated fatty acid are preferred in the practice of this invention.

Most preferred are the sodium and potassium salts of $C_{14}$ to $C_{18}$ unsaturated fatty acids, e.g., sodium oleate and potassium oleate.

The sterols of this invention are those sterols capable of forming liposomes (as described above) with the aliphatic lipids and medicaments of this invention. Among the sterols which may be used are cholesterol, $\beta$-sitosterol, desmosterol, 7-keto-cholesterol, $\beta$-cholestanol, estradiol and the like. Cholesterol and $\beta$-sitosterol are the preferred sterols.

The nature of the medicament to be encapsulated is not critical. Suitable medicaments include vaccines and antigens, as well as drugs. Drugs useful in connection with this invention are those drugs capable of being encapsulated in an aliphatic lipid-sterol-water liposome. The drug delivery system of this invention is especially useful for intestinal absorption of labile drugs.

Among the drugs which may be used in the practice of this invention are insulin, ergot alkaloids, e.g., dihydroergocornine, dihydroergocristine, dihydrooergokryptine, and mixtures thereof, thioridazine, enzymes, hormones, and the like.

Liposomes of this invention may be prepared having the following aliphatic lipid (e.g., sodium or potassium salts of $C_4$ to $C_{18}$ saturated or unsaturated fatty acid)-sterol (e.g., cholesterol)-water weight percent (%) compositions;

Aliphatic lipid from about 0.03% to about 20% sterol from about 1.0% to about 55%, and water from about 45% to about 97%.

Preferably the liposomes may contain the aliphatic lipid from about 1.0% to about 15%, sterol from about 1.0% to about 40%, and water from about 50% to about 97%.

More preferably, the liposomes may contain the aliphatic lipid from about 5.0% to about 10%, sterol from about 1.0% to about 10%, and water from about 75% to about 97%.

The processes of this invention are preferably carried out in an inert atmosphere, e.g., nitrogen, to prevent auto-oxidation of the lipid and/or sterol.

The detergent of this invention does not enter into the final liposome product. Therefore, its selection is not critical. The exception to this is that, it must have sufficient detergent properties under the process conditions of salt concentration, pH and medicament properties not to be a limiting factor in dispersing the proportions of coating lipid and medicament for the liposome formation.

Among the detergents which may be used in the practice of this invention are: anionics such as sodium taurocholate, sodium dodecylsulfate, cholic acid and the like;

Nonionics such as polyethyleneglycol sterol ester (Solulan), polyoxyethylene sorbitan monolaurate (Tween) and the like.

The gel filtration of this invention maybe carried out with gels such as Sephadex, G-10 though G-200, preferably Sephadex G-50 and G-70 (Pharmacia Fine Chemicals, Piscataway, NJ), Sepharase, Agarose, Acrylamide, or Cellulose.

The Processes of this invention may be carried out from a temperature (C.°) at which the critical micelle concentration of the lipid is reached, to about 60° C. Preferably the processes may be carried out at from about 20° C. to about 50° C. More preferably the processes may be carried out at from 25° C. to about 45° C.

When it is necessary to protect the medicament from alkaline degradation, the pH of the liposome system may be adjusted from an alkaline pH to a neutral or acid pH, e.g. from about pH 8 to about pH 5. The pH adjustment may be affected by contacting the liposome system with a pharmaceutically acceptable mineral acid, e.g. hydrochloric acid, organic acid, e.g. citric acid, or buffer solution.

The liposome medicament delivery system of this invention are useful for both oral and parenteral administration of medicaments. Oral administrations is preferred, however, as the liposome encapsulation may serve to protect drugs such as insulin which are labile in the digestive system. For oral administration the liposome suspension may be admixed with pharmacologically acceptable diluents or carriers and with conventional adjuvants such as flavorings and colorings, and administered in such forms as syrups, elixirs, capsules, tablets, etc. Suppositorial administration may also be utilized.

The drawing illustrates a continuous process for producing liposomes using the process teachings of this invention.

A column 10 e.g. chromatography column packed with Sephadex particles 11, has at its discharge end 12 a photoelectric detection means, e.g. a light source 13 and a photoelectric tube 14, and a multidirectional valve 16. The valve 16 is in fluid communication via conduit 17 with a conventional sample fraction collector 18, and via conduit 19 with the loading end 21 of the column 10. A pump 22 on conduit 19 and an introductory circuit 23 complete the external fluid circuitry.

In operation, a drug containing micellar sample, is applied to the Sephadex column 11 and passes down through the column. The light source 13 and photoelectric tube 14 monitor the fractions eluted from the column and send a continuous input signal to a conventional microprocessor 24. Clear solution eluted from the column is continuously recirculated back into the column by valve 16 and pump 22, via conduit 19.

When the milky liposome fraction is detected by the photoelectric tube 14, the microprocessor 24 switches valve 16 to circuit 17 to collect the eluting liposome fractions in the fraction collector 18.

When the liposome fractions have been collected valve 16 is again switched back into fluid communication with circuit 19 for continuous recirculation of the eluting material.

From time to time, additional micellar sample is added by the microprocessor to the column, via introductory circuit 23 and pump 26 from a storage source not shown, to maintain the desired concentration of material on the column. Thus, a continuous process for the production of liposomes is maintained.

In this specification and claims, the following statements are descriptive of the terms indicated:

Micelle—collodial particles, consisting of oriented molecules, e.g., lipid molecules surrounding a medicament.

Liquid crystals—states of matter having characteristics of both liquids and crystalline solids. Liquid crystals are formed when the micelles of a lipid-medicament have penetrated a sterol.

Liposomes—the product of the particle size reduction of liquid crystals.

Lamellae—the layers of a liquid crystal or liposome.

In each of the following examples a clear, mixed micellar sample was applied to a Sephadex G50 column.

The column conditions were:

Type of Column: Sephadex G-50 medium
Column Size: 0.9 cm×48.0 cm
Flow Rate: 1 ml/min.
Volume of Eluted Fraction Collected: 3.0 ml
Elution Buffer: Potassium Phosphate pH 6.0–6.2
The Micellar Sample was 2.0 ml comprising:
Sodium Taurocholate: 10.76 mg/ml
Sodium Oleate: 2.36 mg/ml
Cholesterol: 0.671 mg/ml In each of the examples one of the micellar components was radioactive in order to monitor the fractions eluted from the Sephadex Column. In addition each fraction was visually inspected for turbidity. The micelle fractions are clear solutions while the liposome fractions are milky.

The total radioactivity eluted from the Sephadex column was determined by pipetting 0.1 ml aliquots from each eluted fraction into vials. ACS Liquid Scintillation Fluid was added and the radioactivity determined using a Packard Tri Card Liquid Scintillation Counter. Counts per Minute (CPM) and Disintegrations per Minute (DPM) were determined, with the total DPM indicating total radioactivity.

EXAMPLE I

| Fraction # | CPM | DPM/Fractions | Visual |
|---|---|---|---|
| 1 | 27 | <2 × 's Bkg. | clear |
| 2 | 25 | " | " |
| 3 | 28 | " | " |
| 4 | 31 | 0 | milky |
| 5 | 65 | 1,438 | milky |
| 6 | 46 | 738 | turbid |
| 7 | 154 | 4,712 | " |
| 8 | 2,047 | 74,922 | " |
| 9 | 7,575 | 280,961 | " |
| 10 | 8.126 | 300,077 | clear |
| 11 | 5,961 | 222,446 | " |
| 12 | 2,219 | 81,664 | " |
| 13 | 453 | 15,927 | " |
| 14 | 81 | 1,940 | " |
| 15 | 39 | <2 × 's Bkg. | " |
| 16 | | | " |
| 17 | | | " |
| 18 | | | " |
| 19 | | | " |
| 31 | | | " |
| Bkg. | 26 | TOTAL 984,825 | |

Bkg. = Background radiatiation
$C^{14}$ Na taurocholate 21.52 mg/2 ml = 939,766 DPM Fractions #4 and #5 contain 0.15% of the total $C^{14}$ Na tauracholate eluted from the column. Because of the low CPM value this is considered to be equivalent to 0% $C^{14}$ Na taurocholate.

EXAMPLE II

| Fraction | CPM | DPM/Tube | Visual |
|---|---|---|---|
| 1 | 28 | <2 × Bkg. | clear |
| 2 | 25 | " | " |
| 3 | 28 | " | " |
| 4 | 2,585 | 94,710 | milky |
| 5 | 3,107 | 115,917 | milky |
| 6 | 170 | 5,340 | turbid |
| 7 | 86 | 2,208 | " |
| 8 | 71 | 1,612 | " |
| 9 | 56 | 1,042 | clear |
| 10 | 52 | 896 | |
| 11 | 39 | <2 × Bkg. | |
| 12 | 26 | | |
| 13 | 28 | | |
| 14 | 26 | | |
| 15 | 30 | | |
| 16 | 27 | | |
| | 27 | | |
| 20 | 28 | | |
| Bkg. | 28 | TOTAL 221,725 | |

$C^{14}$ Na Oleate 4.72 mg/2 ml = 349,996 DPM

Fractions #4 and #5 contained 95% of the $C^{14}$ Na Oleate eluted from the column.

EXAMPLE III

| Fraction | CPM | DPM/Fraction | Visual |
|---|---|---|---|
| 1 | 28 | <2 × 's Bkg. | clear |
| 2 | 28 | " | " |
| 3 | 27 | " | " |
| 4 | 1,083 | 39,987 | milky |
| 5 | 521 | 18,661 | milky |
| 6 | 90 | 2,245 | turbid |
| 7 | 81 | 2,032 | " |
| 8 | 67 | 1,471 | " |
| 9 | 49 | <2 × 's Bkg. | clear |
| 10 | 33 | | |
| 11 | 26 | | |
| 12 | 29 | | |
| 13 | 30 | | |
| 14 | 26 | | |
| 15 | 24 | | |
| 16 | 24 | | |
| 17 | 26 | | |
| 18 | 27 | | |
| 19 | 27 | | |
| 20 | 31 | | |
| Bkg. | 27 | | |

$C^{14}$ cholesterol 1.342 mg/2 ml = 48,030 DPM

Fractions #4 and #5 contain 91% of the $C^{14}$ cholesterol eluted from the column.

The results of Examples I, II, and III show the Na taurocholate can be removed by the Sephadex column from mixed micelles. Thus, Na Oleate-cholesterol liposomes were generated.

What is claimed is:

1. A process for the preparation of a liposome medicament delivery system which comprises applying an aqueous micellar medicament-detergent-aliphatic lipid-sterol composition to a gel filtration column, monitoring the column effluent to detect the liposome fraction eluted, and collecting the liposome fraction.

2. The process according to claim 1 wherein the aliphatic lipid is a sodium or potassium salt of a fatty acid having from 4 to 18 carbon atoms, in a lipid concentration which forms micelles above the critical micelle concentration, and wherein the sterol is present in an amount capable of being penetrated by the micelles of the aliphatic lipid.

3. The process according to claim 2 wherein the sodium or potassium salt of the fatty acid has from 14 to 18 carbon atoms.

4. The process according to claim 3 wherein the fatty acid salt is sodium oleate or potassium oleate.

5. The process according to claim 2 wherein the sterol is cholesterol.

6. The process according to claim 5 wherein the sodium or potassium salt of the fatty acid has from about 14 to 18 carbon atoms.

7. The process according to claim 6 wherein the fatty acid salt is sodium or potassium oleate.

8. The process according to claim 2 wherein the detergent is sodium taurocholate.

9. The process according to claim 1 wherein the pH of the liposome system is adjusted by contacting the liposome system with a pharmaceutically acceptable mineral acid, organic acid or buffer solution.

10. A continuous process for the preparation of a liposome medicament delivery system which comprises applying an aqueous micellar medicament-detergent-aliphatic lipid-sterol composition to a gel filtration column, monitoring the column effluent to detect the liposome fraction eluted, continuously recycling the non-liposome effluent from the column, while collecting the liposome fraction.

11. The process according to claim 10 wherein the aliphatic lipid is a sodium or potassium salt of a fatty acid having from 4 to 18 carbon atoms, in a lipid concentration which forms micelles above the critical micelle concentration, and wherein the sterol is present in an amount capable of being penetrated by the micelles of the aliphatic lipid.

12. The process according to claim 11 wherein the sodium or potassium salt of the fatty acid has from 14 to 18 carbon atoms.

13. The process according to claim 12 wherein the fatty acid salt is sodium oleate or potassium oleate.

14. The process according to claim 11 wherein the sterol is cholesterol.

15. The process according to claim 14 wherein the sodium or potassium salt of the fatty acid has from about 14 to 18 carbon atoms.

16. The process according to claim 15 wherein the fatty acid salt is sodium or potassium oleate.

17. The process according to claim 11 wherein the detergent is sodium taurocholate.

18. The process according to claim 10 wherein the pH of the liposome system is adjusted by contacting the liposome system with a pharmaceutically acceptable mineral acid, organic acid or buffer solution.

* * * * *